United States Patent [19]

Womack et al.

[11] Patent Number: 4,554,913
[45] Date of Patent: Nov. 26, 1985

[54] ADJUSTABLE JOINT FOR A KNEE BRACE

[75] Inventors: Darryl L. Womack, Lakewood; Ralph B. Noell, Denver; Larry R. Bradshaw, Arvada, all of Colo.

[73] Assignee: Scott Orthopedics, Inc., Denver, Colo.

[21] Appl. No.: 548,932

[22] Filed: Nov. 7, 1983

[51] Int. Cl.$^4$ .............................................. A61F 3/00
[52] U.S. Cl. ..................................... 128/80 C; 128/88
[58] Field of Search ..................... 128/80 C, 80 F, 88, 128/87 R, 80 R; 3/22, 26

[56] References Cited

U.S. PATENT DOCUMENTS

| | | | |
|---|---|---|---|
| 3,669,105 | 6/1972 | Castiglia | 128/80 C |
| 4,337,764 | 7/1982 | Lerman | 128/80 F |
| 4,372,298 | 2/1983 | Lerman | 128/88 |
| 4,493,316 | 1/1985 | Reed et al. | 128/88 |

OTHER PUBLICATIONS

Catalogue Literature of Pope Brace Company, Kankakee, Ill., p. 9, Publication Date Jul. 1965.

Primary Examiner—John D. Yasko
Assistant Examiner—Christa K. Scott
Attorney, Agent, or Firm—W. Scott Carson

[57] ABSTRACT

An adjustable joint for a knee orthosis or brace. The joint preferably has a polycentric pivot with first and second members having mating, gear teeth and outwardly extending, elongated bars. As one member rotates about its axis, it causes the other member to rotate in an opposite direction about its axis with the bars travelling along respective first and second paths. In the disclosed embodiments, stop members are selectively positioned along the travel paths of the bars with a portion of one in the path of the upper bar which is attached to the thigh engaging component of the brace and a portion of the other in the path of the lower bar attached to the calf engaging component of the brace. The portions of each stop member are preferably eccentrically mounted for rotation about axes spaced from and parallel to the axes of the first and second members of the polycentric pivot. By rotating the stop members about their rotational axes, the eccentric portions thereof can be moved to different locations along the travel paths of the upper and lower bars of the brace. In a second embodiment, stop members are respectively mounted for rotation about the axes of the first and second members of the polycentric pivot. In both embodiments, the stop members are independently and incrementally adjustable in known amounts whereby the travel of the upper and lower bars of the brace can be stopped at any number of predetermined locations.

27 Claims, 9 Drawing Figures

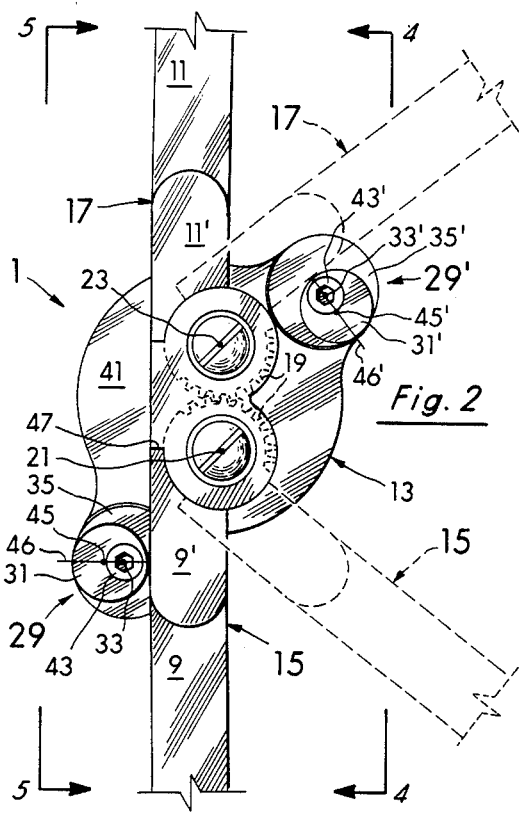
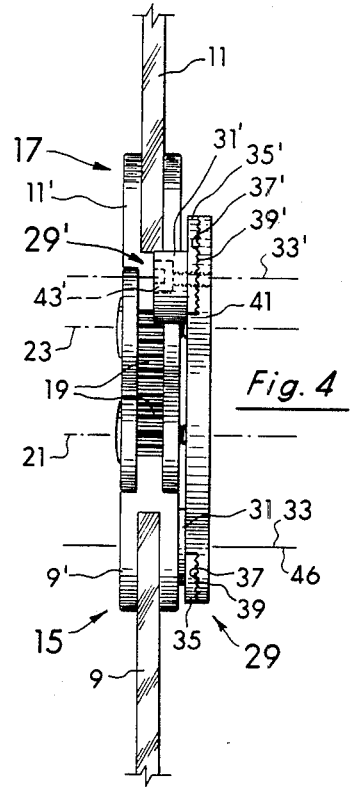
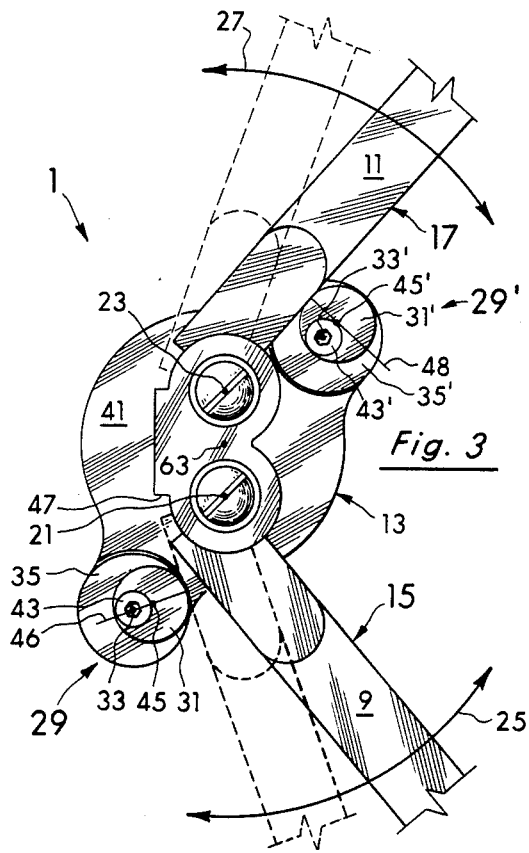
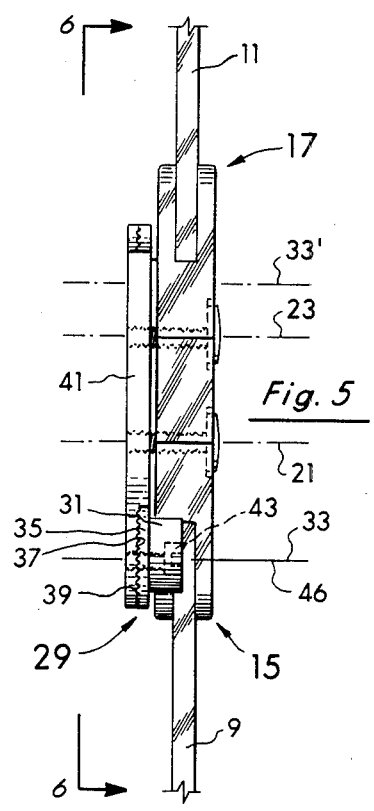

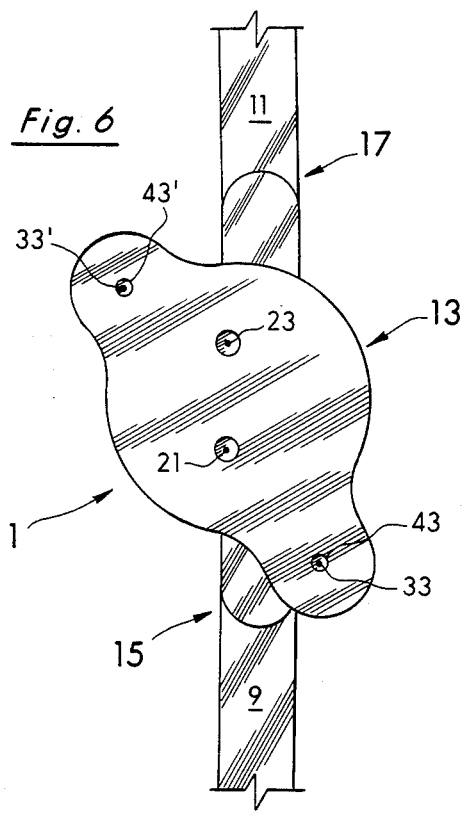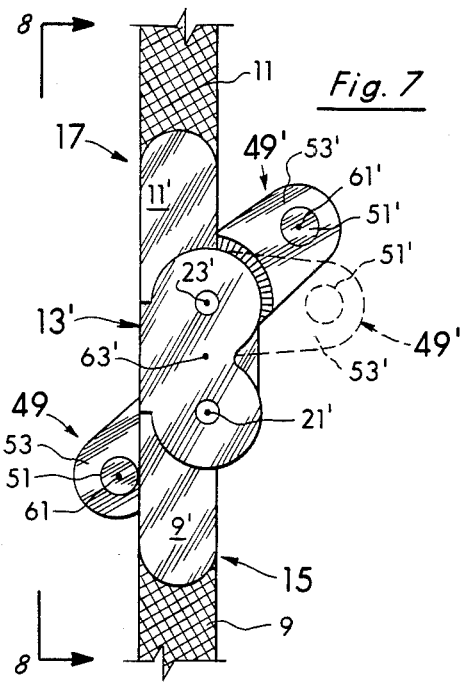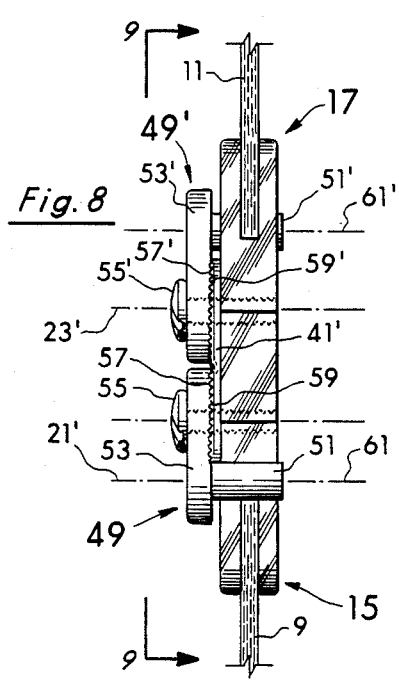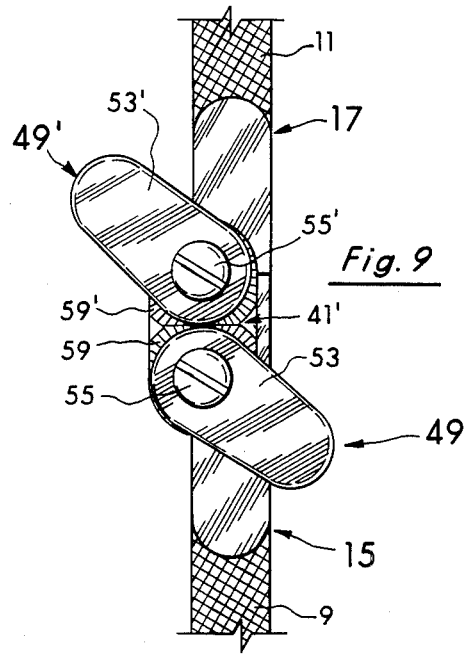

ADJUSTABLE JOINT FOR A KNEE BRACE

FIELD OF THE INVENTION

This invention relates to the field of knee braces and more particularly to the field of adjustable joints for knee braces.

BACKGROUND OF THE INVENTION AND PRIOR ART

Knee orthoses or braces are widely used to provide support for injured and weakened knee joints. Such braces typically include upper and lower bars joined together to pivot about an axis through the knee joint with the upper bar being attached to at high engaging cast or component and the lower one being attached to a calf engaging cast or component. The brace provides support to prevent sideways motion of the knee joint and additionally serves to limit the bending motion of the knee. This limiting is done by controlling the angular travel of the upper and lower bars about the pivotal axis of the brace. In the case of injured or weakened knees that are being strengthened in a rehabilitation program, it is desirable to have a brace with an adjustable range wherein the amount of bending motion of the knee can be gradually increased as the knee joint strengthens.

One of the most widely used knee orthoses is that of U.S. Pat. No. 4,337,764 to Lerman. This brace uses a polycentric pivot and additionally provides an adjustable stop mechanism to control the travel of the pivot. The stop mechanism employs a bracket with an arcuate slot and stop pins. In Lerman's preferred embodiment, the arcuate slot extends beyond the edges of the upper bar of the brace and the stop pins are adjusted to engage opposite edges of the bar to control the angular travel of the upper bar about the pivot. As disclosed, the brace can be modified so that the stop pins engage opposite edges of the lower bar instead of the upper bar if desired. The Lerman stop pins frictionally engage the bracket adjacent the arcuate slot and can be independently and infinitely adjusted along the slot to selectively limit the forward and rearward motion of the knee. In contrast, the adjustable knee joint of the present invention is adjustable in fixed increments due to the use of serrations. In this manner, the allowed motion of the brace of the present invention can be selectively increased or decreased a desired amount (e.g., one degree) by moving the stop member a known number of serrations (e.g., three). Additionally as discussed in more detail herein, the structure of the present knee brace generates relatively small forces on the stop members thereby reducing the risk of accidental displacement or breakage of the stops.

SUMMARY OF THE INVENTION

This invention involves an adjustable joint for a knee orthosis or brace. The joint preferably has a polycentric pivot with first and second members having mating, gear teeth and outwardly extending elongated bars. As one member rotates about its axis, it causes the other member to rotate in an opposite direction about its axis with the bars travelling along respective first and second paths. In both disclosed embodiments of the present invention, stop members can be selectively positioned along the travel paths of the bars with a portion of one stop in the path of the upper bar which is attached to the thigh engaging component of the brace and a portion of the other stop in the path of the lower bar attached to the calf engaging component of the brace.

In the preferred embodiment, the portions of each stop member are eccentrically mounted for rotation about axes spaced from and parallel to the axes of the first and second members of the polycentric pivot. By rotating the stop members about their rotational axes, the eccentric portions thereof can be moved to different locations along the travel paths of the upper and lower bars of the brace. The stop members are mounted to a support bracket and mating, serrated surfaces are provided on the bracket and stop members for incremental adjustment of the stop members in predetermined, known amounts.

In a second embodiment, stop members are respectively mounted for rotation about the axes of the first and second members of the polycentric pivot. Like the preferred embodiment, the stop members are independently and incrementally adjustable in known amounts whereby the travel of the upper and lower bars of the brace can be stopped at any number of predetermined locations.

BRIEF DESCRIPTION OF THE DRAWINGS

FIG. 2 is a view of the adjustable joint of FIG. 1 with the stop members positioned to allow the maximum bending motion between the straight configuration shown in full lines and the deflected configuration shown in dotted lines.

FIG. 3 is a view similar to FIG. 2 showing the stop members in different positions.

FIG. 4 is a view taken along line 4—4 of FIG. 1 showing details of the adjustable joint of the preferred embodiment.

FIG. 5 is a view taken along line 5—5 of FIG. 1 illustrating additional details of the adjustable joint.

FIG. 6 is a rear view of the adjustable joint taken along line 6—6 of FIG. 5.

FIG. 7 is a view similar to FIG. 1 illustrating a second embodiment of the adjustable joint of the present invention.

FIG. 8 is a view taken along line 8—8 of FIG. 7.

FIG. 9 is a view taken along 9—9 of FIG. 8.

DETAILED DESCRIPTION OF THE PREFERRED EMBODIMENTS

Figure 1:
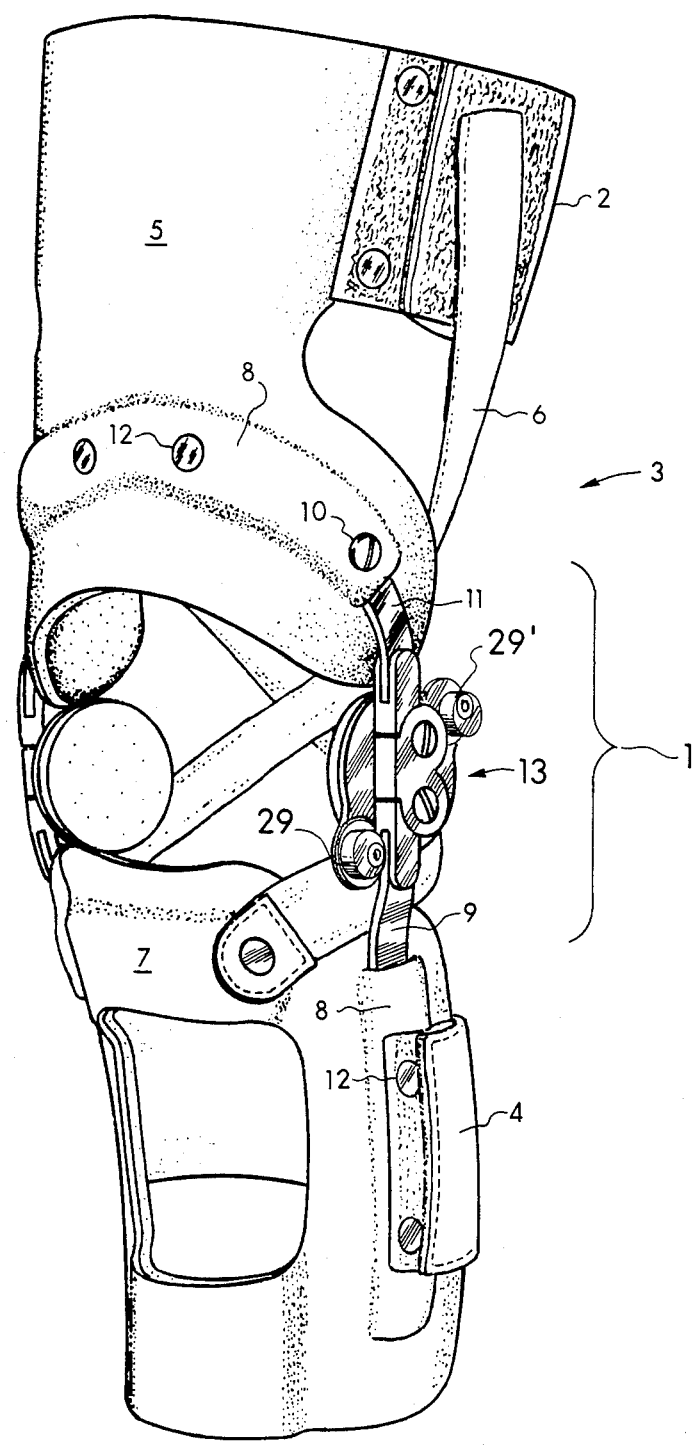
FIG. 1 is a perspective view of a knee brace employing the adjustable joint of the preferred embodiment.

Referring to FIG. 1, the adjustable joint 1 of the present invention is primarily intended for use in a knee orthosis or brace such as 3. Typically, such braces 3 have a thigh engaging component 5 and calf engaging component 7 joined by lower and upper bars 9 and 11 of a pivot such as the illustrated, polycentric pivot 13. The components 5 and 7 are generally secured to the leg of the user by straps such as thigh strap 2 and calf strap 4 with one or more crossing straps 6. The thigh and calf components 5 and 7 can be secured to the respective bars 9 and 11 in any number of ways as, for example, by receiving the ends of the bars 9 and 11 in pockets 8 in the plastic components 5 and 7 and additionally using screws or rivets 10 and 12 as shown in FIG. 1.

The polycentric pivot 13 as best seen in FIGS. 2 and 4 include first and second members 15 and 17. Members 15 and 17 are composed of elongated bars 9 and 11 and attaching yokes 9' and 11'. Each member 15 and 17 at the base of yokes 9' and 11' has gear teeth 19 as best seen in FIGS. 2 and 4. The members 15 and 17 are mounted as illustrated in FIG. 2 for rotation about axes 21 and 23 with the gear teeth 19 mating and the elongated bars 9 and 11 and attaching yokes 9' and 11' extending outwardly of the respective axes 21 and 23.

In a first operational mode of the polycentric pivot 13 as best seen in FIG. 3, rotation of the first member 15 with its elongated bar 9 in a clockwise direction (i.e., from the full line position to the dotted line position) about the axis 21 causes the second member 17 with its elongated bar 11 to rotate about axis 23 in a counterclockwise direction. This movement is as viewed from a common reference point such as a point along either axis 21 or 23 or any point above the plane of FIG. 3. In a second operational mode, rotation of the first member 15 in a counterclockwise direction in FIG. 3 (dotted line position back to the full line position) as viewed from the common reference point causes the second member 17 to rotate about the axis 23 in a clockwise direction. In both operational modes, the elongated bars 9 and 11 and yokes 9' and 11' sweep or move along respective angular paths 25 and 27. This description of the operation of the pivot 13 by initial reference to the member 15 is for illustration only as initial movement of member 17 will likewise cause member 15 to rotate.

As best seen in FIGS. 2 and 3, the pivot 13 of the joint 1 includes stop members 29 and 29'. Each stop member 29 and 29' has a first portion 31 and 31' extending eccentrically about the respective axes 33 and 33'. Each stop member 29 and 29' additionally has a second portion 35 and 35' integral with the first portions 31 and 31' (see FIGS. 2-5). The second portions 35 and 35' extend symmetrically about the respective axes 33 and 33' and each has a serrated surface 37 and 37' (see FIG. 4) which mates with a corresponding serrated surface 39 and 39' on the support bracket 41. The support bracket 41 is fixed in relation to the axes 21 and 23 of the members 15 and 17. By loosening the screws 43 and 43' (see FIGS. 2-5 and in particular screw 43 in FIG. 5 and 43' in FIG. 4), the serrated surfaces 37, 37', 39, and 39' can be separated and the stop members 29 and 29' rotated about the respective axes 33 and 33' (e.g., from the positions shown in FIG. 2 to those of FIG. 3). Once in the desired positions, the stop members 29 and 29' can then again be affixed to support bracket 41 by tightening the screws 43 and 43' to draw the serrated surfaces 37, 37', 39, and 39' into frictional engagement with each other to prevent relative movement.

The eccentric portions 31 and 31' are cylindrical about the respective axes 45 and 45'. The axes 45 and 45' are spaced from and parallel to the axes 33 and 33'. As seen in FIGS. 2 and 4, the elongated portions of members 15 and 17 abut the eccentric portions 31 and 31' along tangents. Also, in extreme positions of FIG. 2, the axes 45 and 45' lie in respective planes 46 and 46' perpendicular to the respective tangents and containing the respective axes 33 and 33'. In this manner, the forces on portions 31 and 31' of the stop members 29 and 29' align with the axes 33 and 33' of the screws 43 and 43' wherein no torque is developed tending to rotate the stop members 29 and 29' away from these positions. The same situation arises with the stop members in their other extreme positions as illustrated by stop member 29 in FIG. 3. In between these extreme positions as shown by stop member 29' in FIG. 3, there is an applied torque along 48; however, the moment arm (i.e., the distance between axes 33' and 45') is very small and the frictional engagement of the surfaces 37 and 39 particularly with the serrations supplies more than enough resistance to firmly affix the stop member 29' in place.

In operation, the stop means 29 and 29' serve to restrict the movement of the members 15 and 17 of the polycentric pivot 13 to within predetermined adjustable limits. As shown in FIG. 2, stop member 29 in one extreme position can abut the first member 15 at the same time the member 15 abuts the part 47 which commonly is present on pivots like 13. Alternately, axis 33 can be moved so that member 15 abuts the stop member 29 in its extreme position before striking part 47 if desired. The size of the eccentric portion 31 and 31' can be varied but the radius of these portions (i.e., about axes 33 and 33') is preferably less than the respective distances between axes 33 and 21 and 33' and 23. Preferably, the radius is as small as possible to reduce any moment arms tending to rotate the stop members 29 and 29' away from their desired positions. The axes 21, 23, 33, and 33' are preferably all fixed relative to each other and parallel to one another.

The serrated surfaces 37, 37', 39' and 39' not only provide strong engagement between the stop members 29 and 29' and the support bracket 41 but also provide calibration for the pivot 13. For example, relative movement of the serrated surfaces for three serrations can be designed to correspond to a one degree change in the swing of bar 9. Alternately, a serration could correspond to a one degree change wherein there would be fewer serrations for increased strength against relative movement when the stop members are fixed in place. Also, although the preferred embodiment provides only a single stop member for each member 15 and 17 with the mating of teeth 19 serving to stop the other member, pairs of stop members could be provided to contact opposite edges of each member 15 and 17 if desired. Additionally, stop members can be provided on both sides of the brace 3 rather than just on the one pivot 13 as shown in FIG. 1.

In FIGS. 7-9, a second embodiment of the invention is disclosed. In this embodiment, the stop members 49 and 49' are mounted for rotation about axes 21' and 23' of the polycentric pivot 13'. As in the preferred embodiment, the stop members 49 and 49' have second portions 53 and 53' which are integral with respective first portions 51 and 51'. In operation and in a manner similar to the preferred embodiment, the screws 55 and 55' (see FIGS. 8 and 9) are loosened to disengage the serrated surfaces 57 and 57' on the second portions from the mating, serrated surfaces 59 and 59 on the support bracket 41'. The stop members 49 and 49' can then be rotated about the respective axes 21' and 23' to the desired positions (see, for example, the dotted position of stop member 49' in FIG. 7). Thereafter, the screws 55 and 55' can be retightened to affix the stop members 49 and 49' in place with the first portions 51 and 51' thereof supported in the desired locations along the angular sweep or travel paths of the elongated portions of members 15 and 17. As in the preferred embodiment, the firt portions 51 and 51' of the stop members 49 and 49' are cylindrical and extend symmetrically about respective axes 61 and 61' which are spaced from and parallel to the axes 21' and 23' of members 15 and 17. As also in the preferred embodiment, the segments of the elongation portions of members 15 and 17 immediately adjacent the pivot 13' are substantially straight. Further, these segments at any one time form a first included angle about the central axis 63' of the pivot 13' in one direction (e.g., clockwise in FIG. 7 from 15 to 17) and a second included angle in an opposite direction (e.g., counterclockwise from 15 to 17). As illustrated in FIG. 7, stop member 49 is positioned in the first included angle and stop member 49' in the second. Similarly, stop member 29 as seen in FIG. 3 is positioned in the first included angle about the central axis of symmetry 63 of pivot 13 and stop member 29' is positioned in the second included angle.

While several embodiments of the invention have been disclosed in detail, it is to be understood that various changes and modifications can be made without departing from the scope of the invention.

We claim:

1. A knee brace comprising:
   a thigh engaging component, a calf engaging component, and means for securing said components respectively to the thigh and calf of a person,
   means for mounting said thigh and calf engaging components to each other, said mounting means including a polycentric pivot having first and second members with mating gear teeth, means for securing one of said membes to said thigh engaging component and the other of said members to the calf engaging component, and means for mounting said first and second members for rotation about respective first and second axes with the respective gear teeth of said first and second members mating whereby rotation of the first member about the first axis causes the second member to rotate about the second axis and rotation of the second member about the second axis causes the first member to rotate about the first axis, said first member further having an elongated portion extending outwardly of the first axis and moving along a first path as said first member rotates about the first axis, and,
   means for restricting the movement of said first member about the first axis, said restricting means including a stop member and means for selectively supporting a portion of said stop member at first and second locations spaced from one another along said first path whereby said first member of said polycentric pivot can rotate about said first axis until said elongated portion thereof abuts said portion of said stop member at either said first or second location, said means for selectively supporting said portion of said stop member including a support member, means for mounting said support member in a fixed position relative to said first and second axes of said polycentric pivot, and means for mounting said portion of said stop member to said support member for selective rotation about a third axis, said portion of said stop member extending eccentrically about said third axis, and said mounting means further including means for selectively affixing said portion of said stop member in fixed non-rotating relationship to said support member at first and second positions about said third axis with said first position defining said first location of said portion of the stop member along said first path and said second position defining said second location of said portion along said first path.

2. The knee brace of claim 1 wherein said eccentric portion of said stop member is substantially cylindrical about an axis spaced from and substantially parallel to said third axis.

3. The knee brace of claim 2 wherein said first and third axes are fixed relative to each other and substantially parallel and the cylinder of said eccentric portion of the stop member has a radius less than the perpendicular distance between said first and third axes.

4. The knee brace of claim 1 wherein said stop member has a second portion integral with said first mentioned portion of said stop member, said second portion extending substantially symmetrically about said third axis and said means for selectively affixing said first portion of said stop member to said support member includes a first surface on said support member, a second surface on said second portion of said stop member, and means for drawing said first and second surfaces into frictional engagement to prevent relative movement of said surfaces.

5. The knee brace of claim 4 wherein said first and second surfaces have mating serrations.

6. The knee brace of claim 1 wherein said affixing means further includes means for incrementally adjusting the position of said portion of said stop member along said first path in predetermined, known amounts about said third axis.

7. The knee brace of claim 1 wherein said first, second, and third axes are fixed relative to each other and substantially parallel, said eccentric portion of said stop member is substantially cylindrical about an axis spaced from and substantially parallel to said third axis, and said elongated portion of said first member abuts the cylinder of said eccentric portion along a tangent.

8. The knee brace of claim 7 wherein said axis of said cylinder lies in a plane perpendicular to said tangent and containing said third axis when said portion of the stop member is in said first position.

9. A knee brace comprising:
   a thigh engaging component, a calf enaging component, and means for securing said components respectively to the thigh and calf of a person,
   means for mounting said thigh and calf engaging components to each other, said mounting means including a polycentric pivot having first and second members with mating gear teeth, means for securing one of said members to said thigh engaging component and the other of said members to the calf engaging component, and means for mounting said first and second members for rotation about respective first and second axes with the respective gear teeth of said first and second members mating whereby in a first operational mode, rotation of the first member in a clockwise direction about the first axis as viewed from a common reference point causes the second member to rotate about the second axis in a counterclockwise direction as viewed from said common reference point and whereby in a second operational mode, rotation of the first member in a counterclockwise direction about the first axis as viewed from said common reference point causes the second member to rotate about the second axis in a clockwise direction as viewed from said common reference point, said first and second members having respective elongated portions extending outwardly of the respective first and second axes and moving along respective first and second paths as said first and second members rotate about the respective first and second axes, and,
   means for restricting the movement of said first and second members about the respective first and second axes, said restricting means including first and second stop members and first means for selectively supporting a portion of said first stop member at first and second locations spaced from each other along said first path, said first supporting means including a support member, means for mounting said support member in a fixed position relative to said first and second axes of said polycentric pivot, and means for mounting said portion of said first stop member to said support member in a fixed, non-rotating relationship, and means for selectively supporting a portion of said second stop member at first and second locations spaced from each other along said second path, said second supporting means including a support member, means for mounting said support member in a fixed position relative to said first and second axes of said polycentric pivot, and means for mounting said portion of said second stop member to said support member in a fixed, non-rotating relationship whereby movement of the polycentric pivot in said first operational mode is stopped when the elongated portion of the first member abuts the first stop member and movement in said second operational mode is stopped when the elongated portion of the second member abuts the second stop member.

10. The knee brace of claim 9 further including means for mounting said portion of said first stop member to said support member for selective rotation about an axis, said mounting means further including means for selectively affixing said portion of said first stop member to said support member at first and second fixed positions about said rotational axis of said portion with said first position defining said first location of said portion of the first stop member along said first path and said second position defining said second location of said portion along said first path.

11. The knee brace of claim 10 wherein the rotational axis of the portion of said first stop member is coincident with said first axis.

12. The knee brace of claim 11 wherein the rotational axis of the portion of said second stop member is coincident with said second axis.

13. The knee brace of claim 10 wherein the rotational axis of the portion of said first stop member is spaced from and substantially parallel to said first axis.

14. The knee brace of claim 13 wherein said portion of said first stop member extends eccentrically about the rotational axis thereof.

15. The knee brace of claim 14 wherein said first axis and the rotational axis of said portion are fixed relative to each other and substantially parallel and said eccentric portion is substantially cylindrical about an axis spaced from and substantially parallel to said rotational axis thereof and the radius of the cylinder of said eccentric portion is less than the perpendicular distance between said first axis and the rotational axis of said eccentric portion.

16. The knee brace of claim 10 wherein said first stop member has a second portion integral with the first portion thereof and said means for selectively affixing said first portion of said first stop member to said support member includes a first surface on said support member, a second surface on said second portion of said first stop member, and means for drawing said first and second surfaces into frictional engagement to prevent relative movement of the surfaces.

17. The knee brace of claim 16 wherein said first and second surfaces have mating serrations.

18. The knee brace of claim 9 wherein said supporting means for the first stop member includes means for incrementally adjusting the position of said portion of the first stop member along said first path in predetermined, known amounts about an axis.

19. The knee brace of claim 9 wherein said portion of said first stop member is substantially cylindrical.

20. The knee brace of claim 19 wherein the cylindrical portion has an axis of symmetry spaced from and substantially parallel to the rotational axis thereof.

21. The knee brace of claim 20 wherein the radius of the cylindrical portion is less than the perpendicular distance between said first axis and the rotational axis of said cylindrical portion.

22. The knee brace of claim 9 wherein said elongated portions have respective substantially straight segments adjacent the respective first and second axes and said polycentric pivot has a central axis with said straight segments extending outwardly of central axis, said straight segments at any one time forming a first included angle therebetween in a first direction about said central axis from one of the segments to the other and a second included angle in a direction opposite to said first direction about said central axis from said one segment to the other, the location of the portion of said first stop member being in said first included angle and the location of the portion of the second stop member being in the second included angle.

23. A knee brace comprising:
a thigh engaging component, a calf engaging component, and means for securing said components respectively to the thigh and calf of a person,
means for mounting said thigh and calf engaging components to each other, said mounting means including a polycentric pivot having first and second members with mating gear teeth, means for securing one of said members to said thigh engaging component and the other of said members to the calf engaging component, and means for mounting said first and second members for rotation about respective first and second axes with the respective gear teeth of said first and second members mating whereby rotation of the first member about the first axis causes the second member to rotate about the second axis and rotation of the second member about the second axis causes the first member to rotate about the first axis, said first member further having an elongated portion extending outwardly of the first axis and moving along a first path as said first member rotates about the first axis, and,
means for restricting the movement of said first member about the first axis, said restricting means including a stop member and means for selectively supporting a portion of said stop member at first and second locations spaced from one another along said first path whereby said first member of said polycentric pivot can rotate about said first axis until said elongated portion thereof abuts said portion of said stop member at either said first or second location, said means for selectively supporting said portion of said stop member including a support member, means for mounting said support member in a fixed position relative to said first and second axes of said polycentric pivot, and means for mounting said portion of said stop member to said support member for selective rotation about said first axis, said portion being spaced from said first axis and said mounting means further including means for selectively affixing said portion of said stop member in non-rotating relationship to said support member at first and second fixed positions about said first axis with said first position defining said first location of said portion of the stop member along said first path and said second position defining said second location of said portion along said first path.

24. The knee brace of claim 23 wherein said stop member has a second portion integral with the first mentioned portion thereof, and said means for selectively affixing said first portion of said first stop member to said support member includes a first surface on said support member, a second surface on said second portion of said stop member, and means for drawing said first and second surfaces into frictional engagement to prevent relative movement of the surfaces.

25. The knee brace of claim 24 wherein said first and second surfaces have mating serrations.

26. The knee brace of claim 23 wherein said affixing means includes means for incrementally adjusting the position of said portion of said stop member along said first path in predetermined, known amounts about said first axis.

27. The knee brace of claim 23 wherein said portion of said first stop member is substantially cylindrical.

* * * * *